(12) United States Patent
Wronski et al.

(10) Patent No.: US 10,588,399 B2
(45) Date of Patent: Mar. 17, 2020

(54) CLEANING APPLIANCE

(71) Applicant: Dyson Technology Limited, Wiltshire (GB)

(72) Inventors: Robert Stefan Wronski, Bristol (GB); Martin Szymon Gutkowski, Swindon (GB); Alexander David May, Swindon (GB)

(73) Assignee: Dyson Technology Limited, Malmesbury, Wiltshire (GB)

(*) Notice: Subject to any disclaimer, the term of this patent is extended or adjusted under 35 U.S.C. 154(b) by 0 days.

(21) Appl. No.: 15/802,895

(22) Filed: Nov. 3, 2017

(65) Prior Publication Data
US 2018/0125221 A1 May 10, 2018

(30) Foreign Application Priority Data
Nov. 4, 2016 (GB) .................................. 1618631.4

(51) Int. Cl.
*A46B 11/00* (2006.01)
*A61C 17/02* (2006.01)
*A61C 17/22* (2006.01)
*A61C 17/36* (2006.01)
A61C 17/028 (2006.01)
A61C 17/28 (2006.01)

(52) U.S. Cl.
CPC .......... *A46B 11/0055* (2013.01); *A61C 17/02* (2013.01); *A61C 17/221* (2013.01); *A61C 17/227* (2013.01); *A61C 17/36* (2013.01); A61C 17/0202 (2013.01); A61C 17/028 (2013.01); A61C 17/28 (2013.01)

(58) Field of Classification Search
CPC .......................... A46B 11/0055; A61C 17/221
See application file for complete search history.

(56) References Cited

U.S. PATENT DOCUMENTS

| 4,534,340 A | 8/1985 | Kerr et al. | |
|---|---|---|---|
| 5,281,137 A * | 1/1994 | Jousson | A61C 17/0202 433/80 |

(Continued)

FOREIGN PATENT DOCUMENTS

| EP | 1 363 760 | 9/2007 |
|---|---|---|
| GB | 2538306 | 11/2016 |

(Continued)

OTHER PUBLICATIONS

Search Report dated Mar. 23, 2017, directed to GB Application No. 1618631.4; 1 page.

(Continued)

*Primary Examiner* — J C Jacyna
(74) *Attorney, Agent, or Firm* — Morrison & Foerster LLP

(57) ABSTRACT

A fluid delivery system of a dental cleaning appliance includes a pump for drawing a working fluid through a fluid inlet, a hydraulic actuator for receiving working fluid from the pump, a drive for actuating the pump, and a nozzle having a fluid outlet for ejecting working fluid from the appliance. The drive includes a motor and a control circuit for operating the motor. The control circuit is configured to detect stalling of the motor in response to the load applied to the pump by the pressurized working fluid stored in the accumulator, and to deactivate the motor when stalling of the motor has been detected.

34 Claims, 11 Drawing Sheets

(56) References Cited

U.S. PATENT DOCUMENTS

| | | | | |
|---|---|---|---|---|
| 5,493,747 | A | * | 2/1996 | Inakagata .......... A61C 17/3418 15/22.1 |
| 5,538,423 | A | * | 7/1996 | Coss .................... A61C 1/0015 408/8 |
| 6,957,925 | B1 | * | 10/2005 | Jacobs ................ A46B 11/001 401/175 |
| 8,522,384 | B2 | | 9/2013 | Leung |
| 2002/0058231 | A1 | * | 5/2002 | Friedman ................ A61C 5/62 433/90 |
| 2003/0089695 | A1 | * | 5/2003 | Furtwangler ...... A61C 13/0028 219/227 |
| 2004/0076549 | A1 | | 4/2004 | Tegeler et al. |
| 2005/0238412 | A1 | | 10/2005 | Jacobs et al. |
| 2005/0272001 | A1 | | 12/2005 | Blain et al. |
| 2008/0193566 | A1 | * | 8/2008 | Miller ................ A61B 1/00135 424/718 |
| 2008/0254408 | A1 | * | 10/2008 | Coates .................. A61C 15/00 433/122 |
| 2015/0196374 | A1 | * | 7/2015 | Fusi, II ............. A61C 17/0211 433/80 |
| 2017/0042648 | A1 | * | 2/2017 | Zachar ............... A61C 17/0208 |

FOREIGN PATENT DOCUMENTS

| | | |
|---|---|---|
| JP | 6-80394 | 11/1994 |
| JP | 10-57773 | 3/1998 |
| JP | 11-128252 | 5/1999 |
| JP | 2004-173466 | 6/2004 |
| JP | 2009-234440 | 10/2009 |
| WO | WO-2007/025244 | 3/2007 |
| WO | WO-2008/001303 | 1/2008 |
| WO | WO-2013/095462 | 6/2013 |
| WO | WO-2014/140979 | 9/2014 |
| WO | WO-2014/203451 | 12/2014 |
| WO | WO-2015/113872 | 8/2015 |

OTHER PUBLICATIONS

Further Search Report dated Apr. 20, 2017, directed to GB Application No. 1618631.4; 2 pages.

International Search Report and Written Opinion, dated Dec. 7, 2017, directed to International Application No. PCT/GB2017/053194; 11 pages.

Notice of Reasons for Rejection dated Jan. 28, 2019, directed to JP Application No. 2017-212588; 12 pages.

* cited by examiner

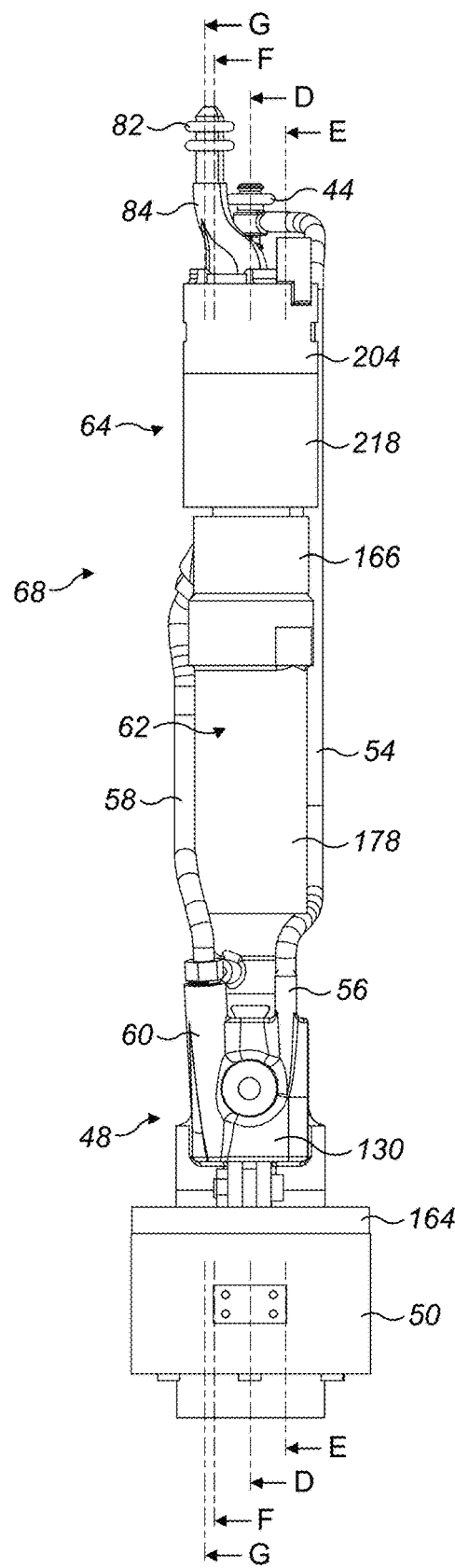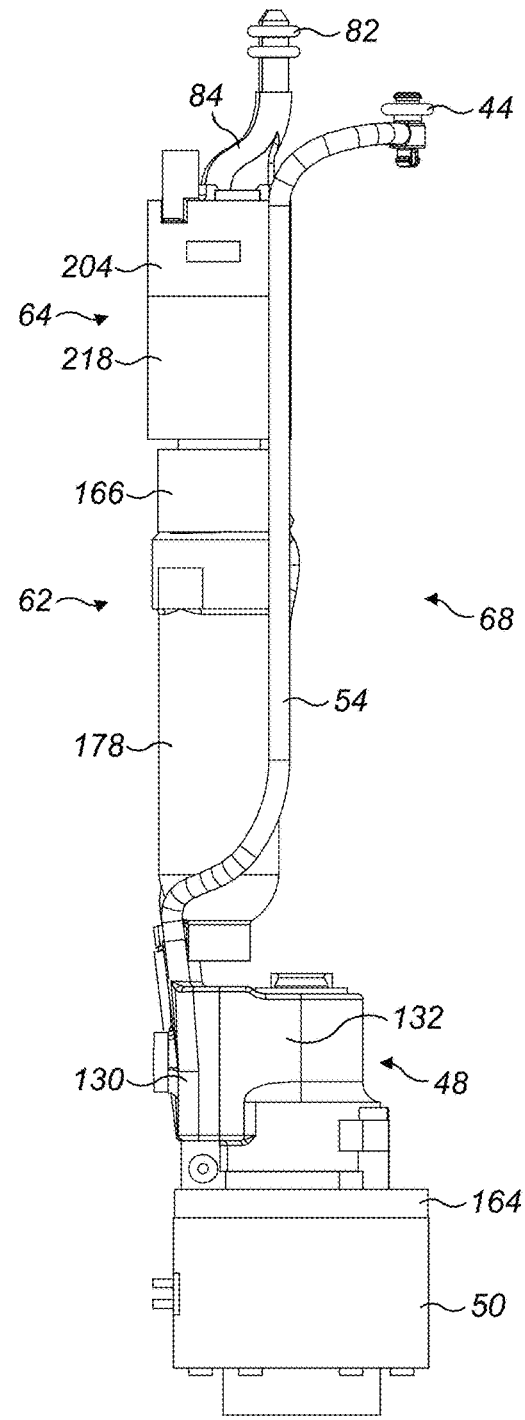
FIG. 7
FIG. 8

CLEANING APPLIANCE

REFERENCE TO RELATED APPLICATIONS

This application claims the priority of United Kingdom Application No. 1618631.4, filed Nov. 4, 2016, the entire contents of which are incorporated herein by reference.

FIELD OF THE INVENTION

The present invention relates to a cleaning appliance. The cleaning appliance is preferably a handheld cleaning appliance, and is preferably a surface treating appliance. In preferred embodiments of the invention, the appliance is a dental cleaning appliance. In a preferred embodiment, the appliance is an electric toothbrush having a fluid delivery system for delivering a fluid to the teeth of the user. This fluid may be toothpaste, or a fluid for improved interproximal cleaning. Alternatively, the appliance may not include any bristles or other elements for brushing teeth, and may be in the form of a dedicated interproximal cleaning appliance.

BACKGROUND OF THE INVENTION

Electric toothbrushes generally comprise a cleaning tool which is connected to a handle. The cleaning tool comprises a stem and a brush head bearing bristles for brushing teeth. The brush head comprises a static section which is connected to the stem, and at least one moveable section which is moveable relative to the static section, for example with one of a reciprocating, oscillating, vibrating, pivoting or rotating motion, to impart a brushing movement to bristles mounted thereon. The stem houses a drive shaft which couples with a transmission unit within the handle. The transmission unit is in turn connected to a motor, which is driven by a battery housed within the handle. The drive shaft and the transmission unit convert rotary or vibratory motion of the motor into the desired movement of the moveable section of the brush head relative to the static section of the brush head.

It is known to incorporate into an electric toothbrush an assembly for generating a jet of fluid for interproximal cleaning. For example, U.S. Pat. No. 8,522,384 describes an electric toothbrush in which the handle of the toothbrush defines a fluid chamber for storing a liquid such as water, and a slidable cover for enabling the fluid chamber to be accessed for replenishment by a user. A fluid path connects the fluid chamber to a nozzle located on a static portion of the brush head. A pump located within the fluid path is actuated upon user operation of an actuator on the handle to pump fluid from the fluid chamber to the nozzle for release under pressure from the nozzle.

SUMMARY OF THE INVENTION

In a first aspect, the present invention provides a dental cleaning appliance comprising: a fluid delivery system comprising a fluid inlet, a positive displacement pump for drawing a working fluid through the fluid inlet, a drive for actuating the pump, and a nozzle having a fluid outlet for ejecting working fluid from the appliance wherein the drive comprises a stepper motor for driving the pump.

The drive preferably comprises a stepper motor, and a control circuit for operating the motor. The drive preferably further comprises a linear actuator coupled to the motor, the control circuit being configured to drive the motor to move the actuator. In a preferred embodiment, the actuator is in the form of a drive rod, which moves along a linear path. The motor is preferably a linear stepper motor.

The positive displacement pump preferably comprises a fluid displacement member which is moveable by the drive relative to a chamber of the pump to draw fluid into the chamber, and to subsequently urge a burst of fluid from the chamber. The fluid displacement member is preferably moveable along a linear path relative to the chamber. In a preferred embodiment, the positive displacement pump is in the form of a piston pump, in which the fluid displacement member is a piston which is reciprocally movable within the chamber between a first position and a second position to draw fluid into the fluid chamber and to urge fluid from the fluid chamber.

The pump may be a double acting pump, in which, in each stroke of the fluid displacement member, a first volume of fluid is drawn into the pump and a second volume of fluid is urged from the pump. In a preferred embodiment, the pump is a double acting piston pump, in a piston divides a chamber of the pump into first and second fluid chambers. As the piston moves in a given direction relative to the chamber, working fluid is drawn into one of the fluid chambers, and, simultaneously, working fluid is expelled from the other fluid chamber.

The control circuit is preferably configured to detect stalling of the motor, and to deactivate the motor when stalling of the motor has been detected. For example, the appliance may comprise a fluid chamber for receiving working fluid from the pump. The appliance may further comprise a valve having an open position for enabling a burst of working fluid to be delivered from the fluid chamber to the nozzle, and a closed position for enabling the fluid chamber to be replenished under the action of the pump. As the working fluid enters the fluid chamber, the pressure of the working fluid stored within the fluid chamber, and thus the pressure of the fluid which is urged from the pump into the fluid chamber, increases. This in turn increases the load on the motor of the drive, which will stall when the load on the motor increases above its design limits. Upon detection the stalling of the motor, the control circuit can deactivate the motor. This can allow the pressure at which working fluid is stored in the fluid chamber to be controlled without requiring a separate sensor to detect the pressure of the working fluid stored in the fluid chamber.

In a second aspect, the present invention provides a dental cleaning appliance comprising: a fluid delivery system comprising a fluid inlet, a pump for drawing a working fluid through the fluid inlet, a drive for actuating the pump, and a nozzle having a fluid outlet for ejecting working fluid from the appliance; and wherein the drive comprises a motor and a control circuit for operating the motor, and wherein the control circuit is configured to detect stalling of the motor and to deactivate the motor when stalling of the motor has been detected The motor is preferably configured to stall when the pressure of pumped working fluid, and thus the pressure of working fluid within the fluid chamber, is in the range from 3 to 10 bar, preferably in the range from 5 to 8 bar, and in a preferred embodiment is around 6.5 bar. For example, a limit to the current which may be drawn by the motor may be set, for example in a motor controller of the control circuit, with the stalling occurring at a pressure which is determined by the set current limit and the motor design. The pressure at which the motor stalls may be adjusted by changing the current limit set by the motor controller.

The control circuit may be configured to detect stalling of the motor from a voltage generated by the motor. The control circuit may be arranged to measure a back electromotive force (back emf) across a coil or coils of the motor, and to deactivate the motor depending on the measured back emf. Alternatively, depending on the nature of the motor the control circuit may be configured to detect stalling of the motor from a current drawn by the motor, for example where the motor is a brushed dc motor.

The fluid delivery system is preferably arranged to deliver working fluid to the teeth of the user in the form of discrete bursts of working fluid. The capacity of the fluid chamber may be substantially the same as the volume of a single burst of working fluid. For example, the fluid chamber may have a capacity of around 0.25 ml, and a single burst of working fluid may have a volume of around 0.25 ml. In this case, the fluid chamber is substantially emptied following the delivery of a single burst of working fluid to the nozzle, and so requires replenishment before another burst of working fluid can be delivered. The time taken to replenish the accumulator is preferably in the range from 0.25 to 1 second, and is preferably around 0.5 seconds, during which time the control circuit is preferably arranged to inhibit the delivery of working fluid to the nozzle.

Alternatively, the capacity of the fluid chamber may be larger than the volume of a single burst of working fluid. For example, the fluid chamber may have a capacity of around 0.75 ml, and a single burst of working fluid may have a volume of around 0.25 ml. In this case, the valve is held in an open position by the control circuit for a time required for a selected volume of working fluid to be ejected from the fluid chamber. For example, the valve may be held in an open position for a time period in the range from 1 to 100 ms, more preferably in the range from 5 to 50 ms, and in a preferred embodiment for a time period of 30 ms, to allow a single burst of working fluid having a volume of 0.25 ml to be delivered to the nozzle.

The appliance preferably comprises a hydraulic accumulator, which in turn comprises the fluid chamber which is supplied with working fluid from the pump. The accumulator is preferably a gas-charged accumulator, although the accumulator may be a spring-driven accumulator.

The valve is preferably located downstream from the fluid chamber. The control circuit is preferably configured to control the position of the valve. The valve is preferably a solenoid valve. The valve may be opened to allow the fluid chamber to be substantially drained of working fluid when a single burst of working fluid is delivered to the teeth of a user. Alternatively, the valve may be opened for a period of time which allows only a part of the fluid which is stored in the fluid chamber to be delivered to the teeth of a user. For example, the fluid chamber may be sized to accommodate sufficient working fluid for a plurality of bursts of working fluid, and the valve may be opened for a period of time which allows a desired amount of working fluid to be ejected from the nozzle.

The appliance preferably comprises a fluid reservoir for storing working fluid, and wherein the pump is arranged to draw working fluid from the fluid reservoir. The fluid reservoir preferably has a capacity in the range from 5 to 50 ml.

In a third aspect, the present invention provides a dental cleaning appliance comprising a fluid delivery system comprising a fluid inlet, a pump for drawing a working fluid through the fluid inlet, a hydraulic actuator for receiving working fluid from the pump, a drive for actuating the pump, and a nozzle having a fluid outlet for ejecting working fluid from the appliance, wherein the drive includes a motor and a control circuit for operating the motor, the control circuit being configured to detect stalling of the motor in response to the load applied to the pump by the pressurized working fluid stored in the accumulator, and to deactivate the motor when stalling of the motor has been detected.

The appliance is preferably a handheld appliance, in which the pump and the accumulator are located in a handle of the appliance.

The appliance may be in the form of a dedicated interproximal cleaning appliance for cleaning between the gaps in the user's teeth. Alternatively, the appliance may be in the form of a toothbrush which has the additional function of improved interproximal cleaning through the emission of a burst of working fluid into the interproximal gap. As the nozzle is moved between adjacent teeth of the user, the user may depress a button of a user interface provided on a handle of the appliance to actuate the valve to cause a burst of working fluid to be ejected from the nozzle. Alternatively, the appliance may be configured to actuate the delivery of working fluid to the teeth of the user automatically depending on the magnitude of an output from a sensor for detecting that the nozzle is located within an interproximal gap. For example, the sensor may be in the form of a light detector, such a camera or a light sensor, for receiving light, such a visible light or infrared light, reflected from a user's teeth. As another alternative, the appliance may be configured to actuate the delivery of working fluid to the teeth of the user automatically at a fixed frequency, for example between 0.5 and 5 Hz.

Features described above in connection with the first aspect of the invention are equally applicable to the second and third aspects of the invention, and vice versa.

BRIEF DESCRIPTION OF THE DRAWINGS

Preferred features of the present invention will now be described by way of example only with reference to the accompanying drawings, in which:

FIG. 7 is a front view of the first part of the fluid delivery system;

FIG. 8 is a side view of the first part of the fluid delivery system;

DETAILED DESCRIPTION OF THE INVENTION

Figure 1A:
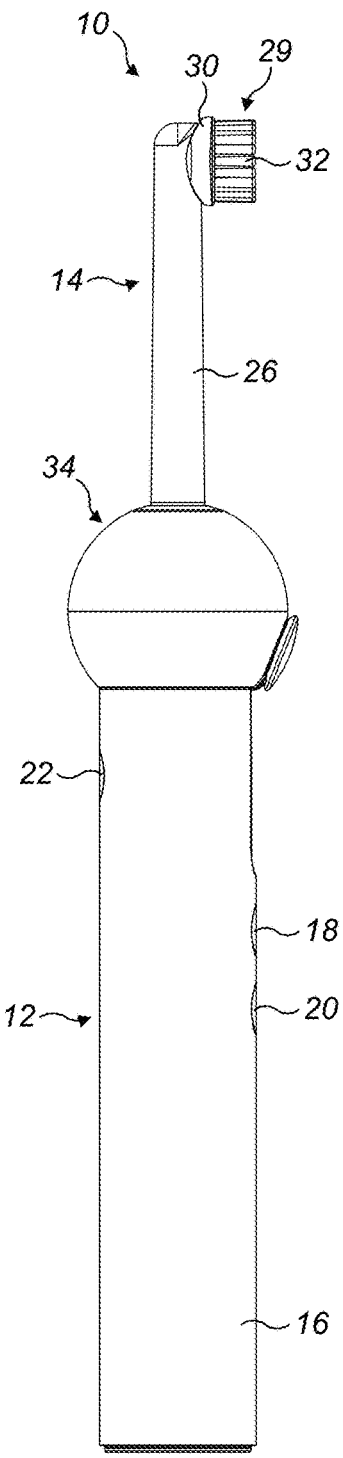
FIG. 1(a) is a right side view of a dental cleaning appliance.
Figure 1B:
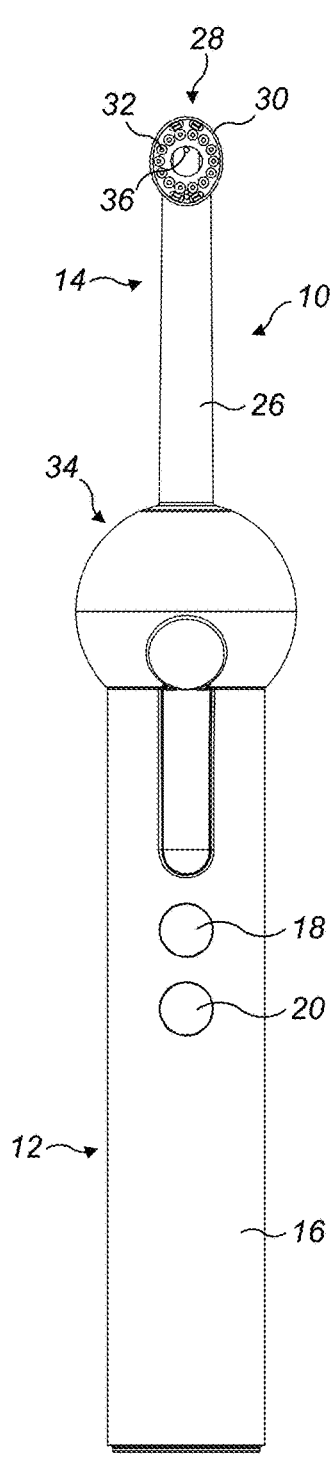
FIG. 1(b) is a front view of the appliance.
Figure 1C:
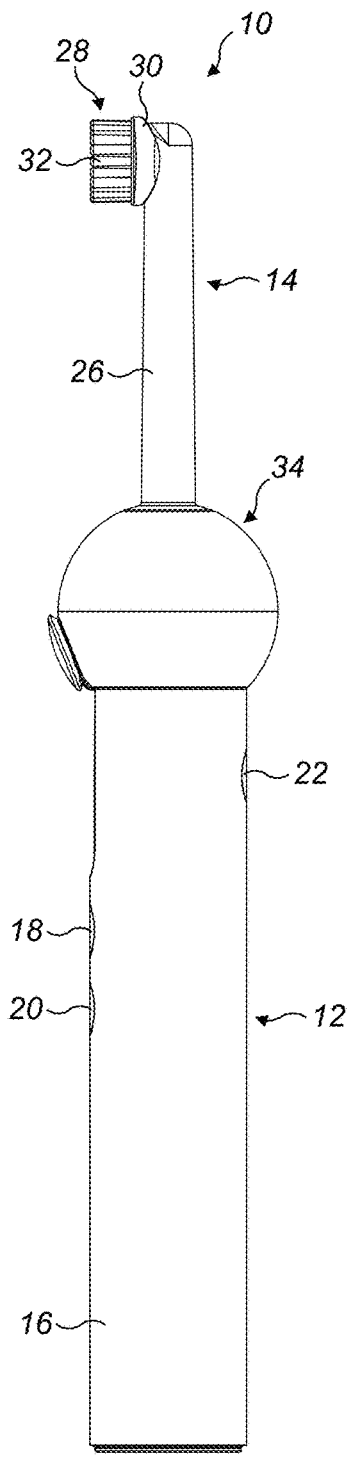
FIG. 1(c) is a left side view of the appliance.

FIGS. 1(a) to 1(c) illustrate external views of an embodiment of a dental cleaning appliance 10. In this embodiment, the appliance is in the form of a handheld appliance, which is in the form of an electric toothbrush having an integrated assembly for dispensing a working fluid for improved interproximal cleaning.

The appliance 10 comprises a handle 12 and a cleaning tool 14. The handle 12 comprises a body 16 which is gripped by a user during use of the appliance 10. The body 16 is preferably formed from plastics material, and is preferably generally cylindrical in shape. The handle 12 comprises a plurality of user operable buttons 18, 20, 22 which are located within respective apertures formed in the body 16 so as to be accessible to the user.

The cleaning tool 14 comprises a stem 26 and a head 28. The stem 26 is elongate in shape, which serves to space the head 28 from the handle 12 to facilitate user operability of the appliance 10. In this embodiment, the head 28 of the cleaning tool 14 comprises a brush unit, which comprises a bristle carrier 30 and a plurality of bristles 32 mounted on the bristle carrier 30. However, in other embodiments the cleaning tool 14 may be provided without a brush unit so that the appliance is in the form of a dedicated interproximal cleaning appliance for cleaning between the gaps in the user's teeth.

The cleaning tool 14 also comprises a fluid reservoir 34 for storing a working fluid, and a nozzle 36 for delivering one or more bursts of working fluid to the teeth of the user during use of the appliance 10. The fluid reservoir 34 is connected to the stem 26, and preferably extends at least partially around the stem 26. In this embodiment which includes a brush unit, the brush unit extends at least partially around the nozzle 36.

The nozzle 36 forms part of a fluid delivery system 40 for receiving working fluid from the fluid reservoir 34 and for delivering bursts of working fluid to the teeth of a user during use of the appliance 10. In this embodiment, the working fluid is a liquid working fluid, which is preferably water. Each burst of working fluid preferably has a volume which is less than 1 ml, more preferably less than 0.5 ml, and in this example is around 0.25 ml. The tip of the nozzle 36 comprises a fluid outlet 42 through which a burst of working fluid is delivered to the teeth of the user.

Figure 2:
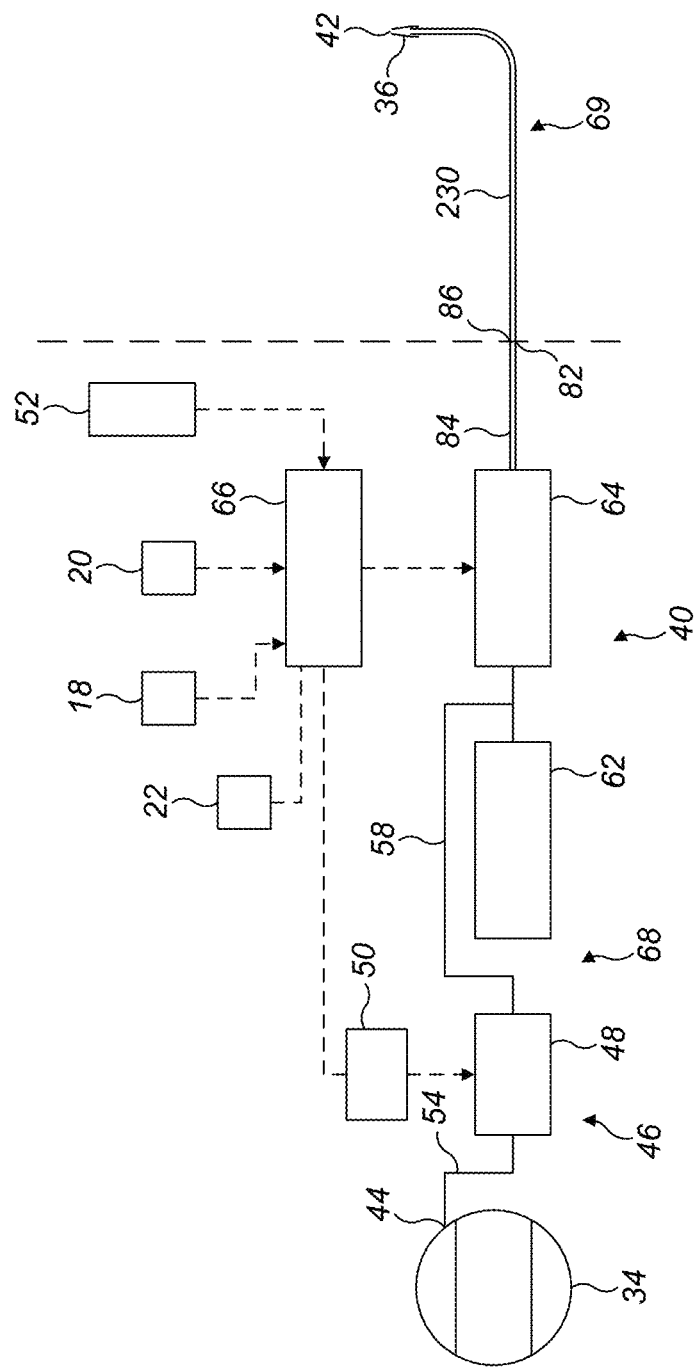
FIG. 2 illustrates schematically components of a fluid delivery system for delivering a burst of a working fluid to the teeth of a user.

The fluid delivery system 40 is illustrated schematically in FIG. 2. In overview, the fluid delivery system 40 comprises a fluid inlet 44 for receiving working fluid from the fluid reservoir 34, and a pump assembly 46 for drawing working fluid from the fluid reservoir 34 through the fluid inlet 44. The pump assembly 46 is located within the handle 12. As discussed in more detail below, the pump assembly 46 comprises a positive displacement pump 48 and a drive for driving the pump 48. The drive comprises a stepper motor 50, preferably a linear stepper motor, and a linear actuator connected to the motor 50. A battery 52 for supplying power to the motor 50 is also located in the handle 12. The battery 52 is preferably a rechargeable battery.

A first conduit 54 connects the fluid inlet 44 of the fluid delivery system 40 to a fluid inlet 56 of the pump 48. A second conduit 58 connects a fluid outlet 60 of the pump 48 to a hydraulic accumulator 62. A solenoid valve 64 is located downstream from the accumulator 62. A control circuit 66 controls the actuation of the motor 50, and so the motor 50 and the control circuit 66 provide a drive for driving the pump 48. The battery 52 supplies power to the control circuit 66. The control circuit 66 includes a motor controller, which supplies power to the motor 50. The control circuit 66 also controls the movement of the solenoid valve 64 between a closed position, which is adopted when working fluid is being delivered to the accumulator 62 by the pump 48, and an open position, which is adopted to effect the delivery of a burst of working fluid from the accumulator 62 to the nozzle 36.

In this embodiment, the control circuit 66 receives signals generated when the user depresses the buttons 18, 20, 22 located on the handle 12 of the appliance 10. Alternatively, or additionally, the control circuit 66 may receive signals which are generated by a sensor located within the appliance, or which are received from a remote device, such as a display or a personal device. For brevity, in the following description the control circuit 66 receives signals which are generated when the user operates one of the buttons 18, 20, 22.

The fluid inlet 44, the pump assembly 46, the accumulator 62 and the solenoid valve 64 are located in the handle 12. In other words, a first part 68 of the fluid delivery system 40 is located in the handle 12, and a second part 69 of the fluid delivery system 40 is located in the cleaning tool 14.

Figure 3:
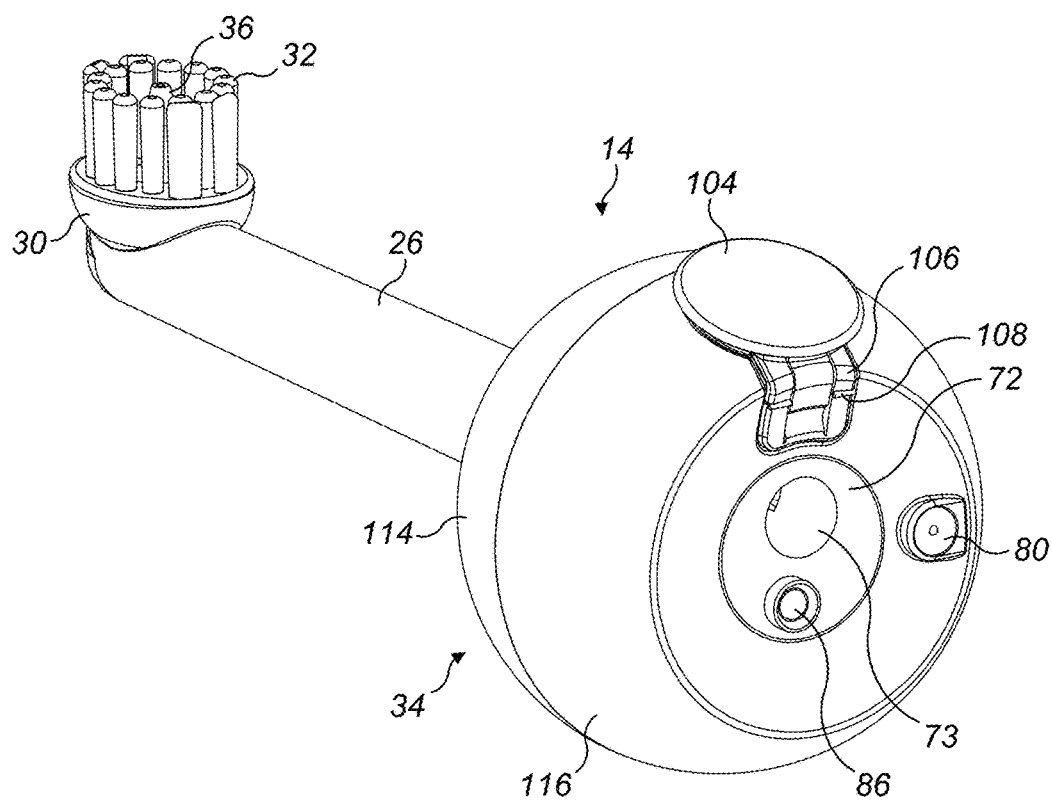
FIG. 3 is a right side perspective view, from above, of a cleaning tool of the appliance.
Figure 4:
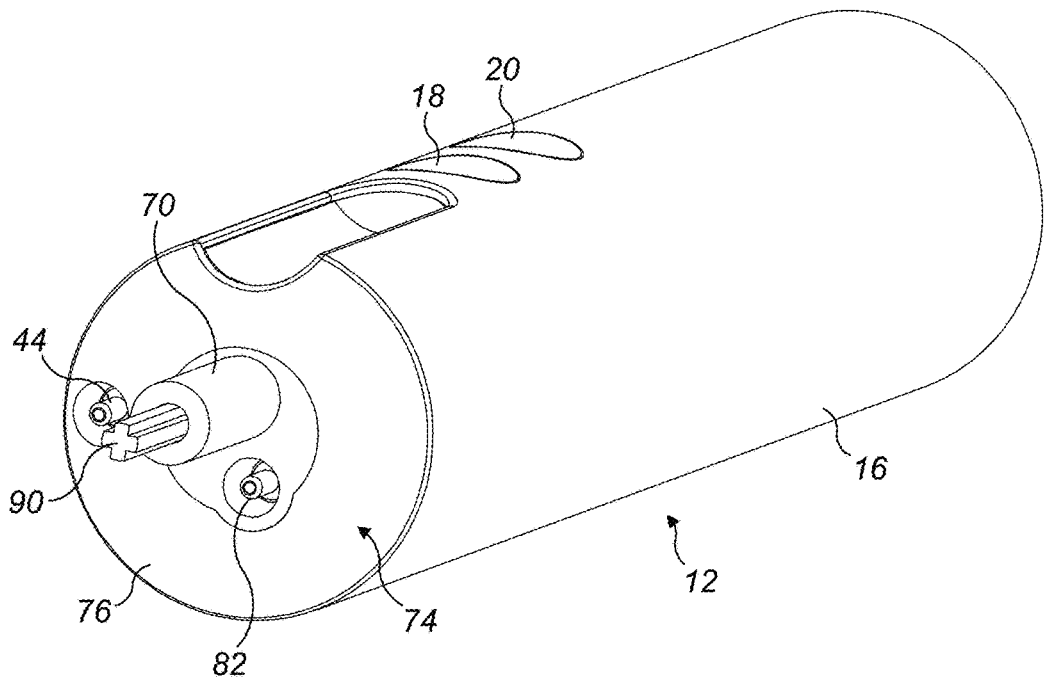
FIG. 4 is a right side perspective view, from above, of a handle of the appliance.
Figure 5:
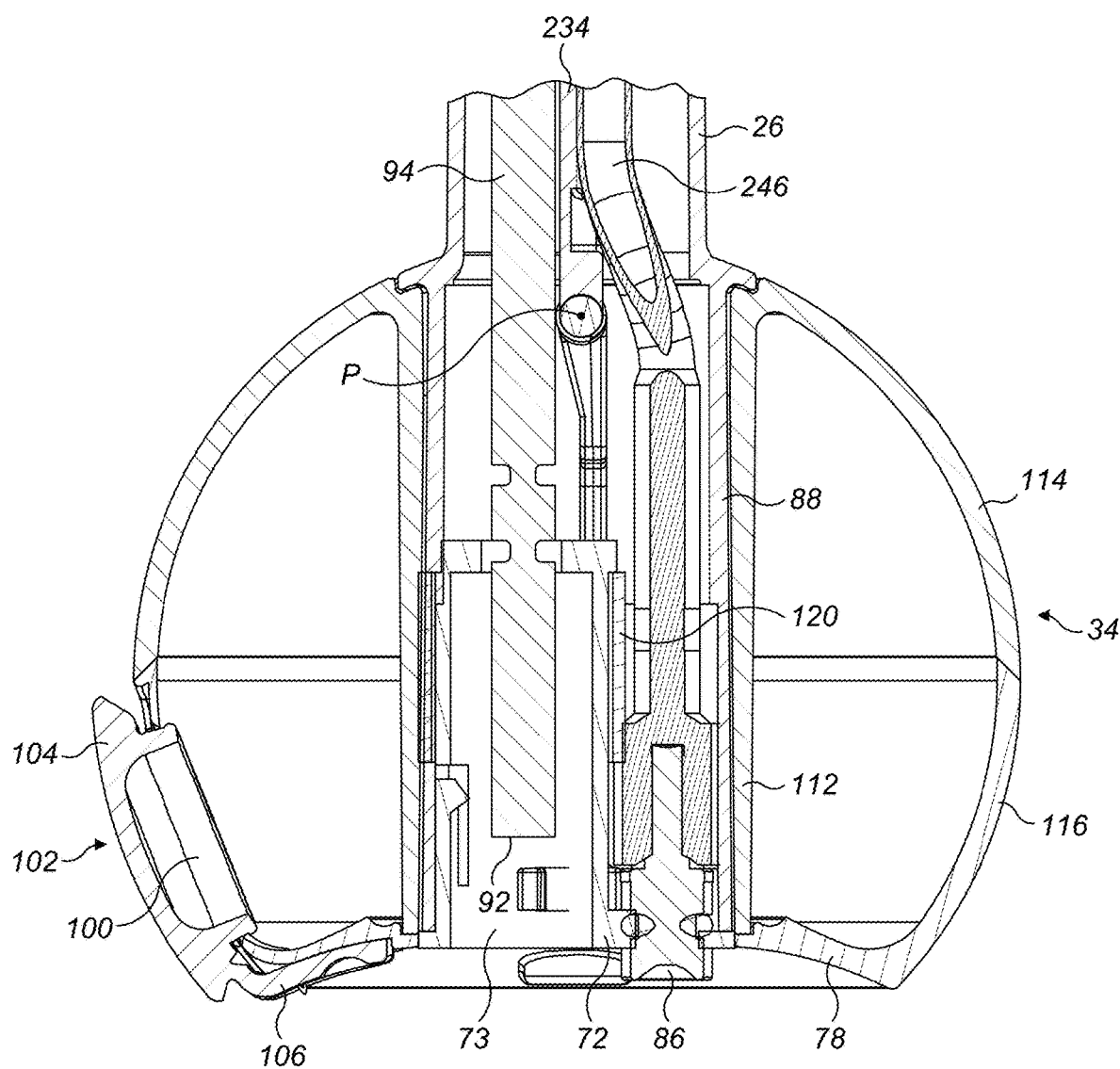
FIG. 5 is a side sectional view of a lower part of the cleaning tool.
Figure 6:
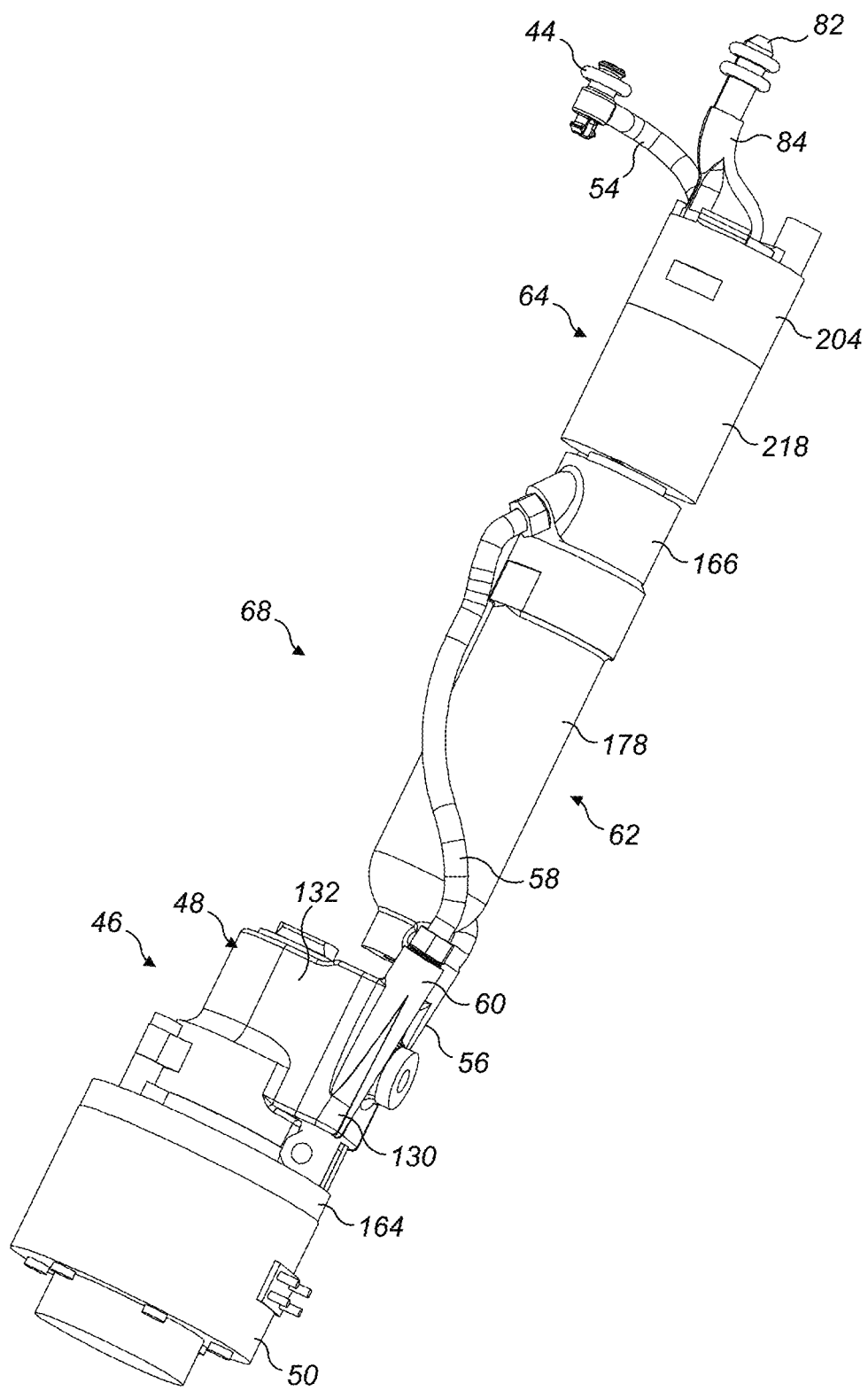
FIG. 6 is a perspective view of a first part of the fluid delivery system which is located in the handle of the appliance.
Figure 9:
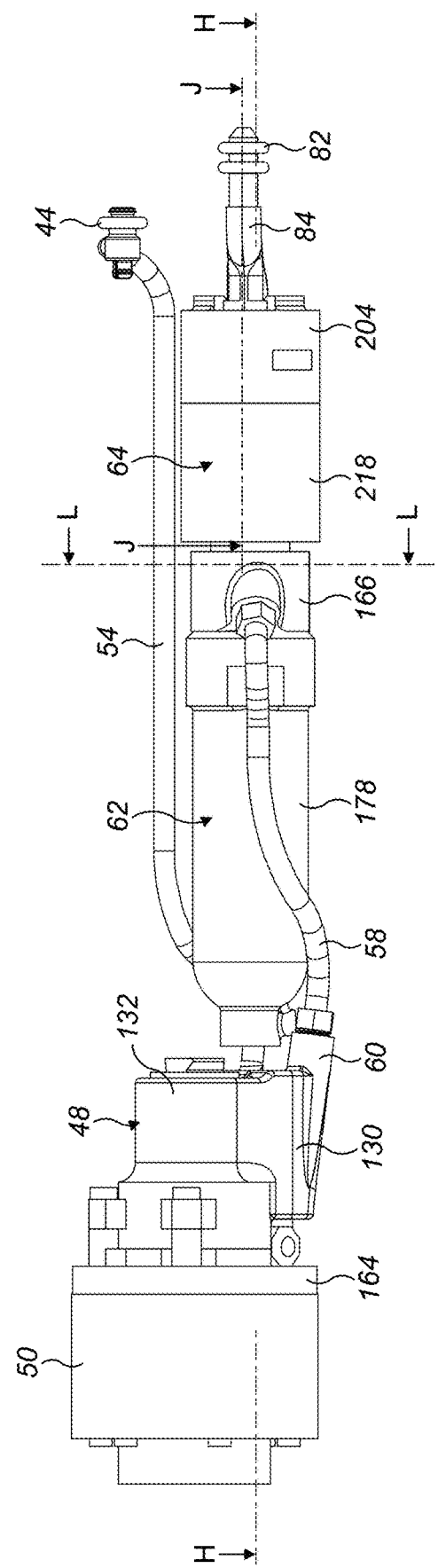
FIG. 9 is a rear view of the first part of the fluid delivery system.

The cleaning tool 14 is detachably connected to the handle 12. With reference to FIGS. 3 to 5, the handle 12 comprises a male connector, preferably in the form of a spigot 70, which is received by a complementary female connector, preferably in the form of a recessed connector 72, of the cleaning tool 14. The recessed connector 72 defines a generally cylindrical recess 73 for receiving the spigot 70. The spigot 70 preferably protrudes outwardly from an end wall 74 of the body 16, and preferably in a direction which is parallel to a longitudinal axis of the handle 12. The end wall 74 defines an annular seat 76 for receiving an annular bottom wall 78 of the fluid reservoir 34 when the cleaning tool 14 is mounted on the handle 12. The annular seat 76 comprises the fluid inlet 44 of the fluid delivery system 40. The fluid inlet 44 receives fluid from a reservoir fluid outlet port 80 of the fluid reservoir 34 when the cleaning tool 14 is mounted on the handle 12. The handle 12 comprises a handle fluid outlet port 82 located adjacent to the spigot 70, and which is connected to an outlet from the solenoid valve 64 by a third conduit 84 located in the handle 12. The cleaning tool 14 comprises a cleaning tool fluid inlet port 86 for receiving fluid from the handle fluid outlet port 82 when the cleaning tool 14 is connected to the handle 12. The cleaning tool fluid inlet port 86 protrudes from the base of the recessed connector 72. The recessed connector 72 is housed within, and connected to, a relatively wide base section 88 of the stem 26.

As mentioned above, the cleaning tool 14 includes a bristle carrier 30 which is moveable relative to the stem 26. The appliance 10 comprises a drive mechanism for driving the movement of the bristle carrier 30 relative to the stem 26. The drive mechanism comprises a transmission unit connected to the bristle carrier 30, and a drive unit for driving the transmission unit to move the bristle carrier 30 relative to the stem 26. The handle 12 comprises the drive unit of the drive mechanism. The drive unit comprises a motor, preferably in the form of a dc motor, which is actuated by the control circuit 66 in response to the user depression of one or more of the buttons of the handle 12. The motor of the drive unit is connected via a gear train to a rotatable drive unit coupling member 90 which protrudes outwardly from the spigot 70, and which rotates relative to the body 16 upon actuation of the motor of the drive unit. The cleaning tool 14 comprises the transmission unit of the drive mechanism. The transmission unit comprises a transmission unit coupling member 92 which couples with, and preferably receives, the drive unit coupling member 90 when the cleaning tool 14 is connected to the handle 12. The transmission unit coupling member 92 is connected to, and is preferably integral with, one end of a connecting rod 94 housed within the stem 26. The other end of the connecting rod 94 is connected to the side surface of the bristle carrier 30 so that periodic rotation of the connecting rod 94 about a 15° angle results in a 15° sweeping movement of the bristle carrier 30 relative to the stem 26.

As mentioned above, the fluid reservoir 34 is mounted on, and extends at least partially around, the stem 26 of the cleaning tool 14. In this embodiment, the fluid reservoir 34 is annular in shape, and so surrounds the stem 26. The fluid reservoir 34 is preferably located at or towards the end of the stem 26 which is remote from the head 28, and so in this embodiment extends around the base section 88 of the stem 26. The fluid reservoir 34 preferably has a capacity in the range from 5 to 50 ml, and in this embodiment has a capacity of 25 ml.

The fluid reservoir 34 is filled through a reservoir fluid inlet port 100 formed in the external wall of the fluid reservoir 34. The fluid inlet port 100 is preferably formed in an annular external side wall of the fluid reservoir 34. The reservoir fluid inlet port 100 is sealed by a closure member 102. The closure member 102 is moveable relative to the fluid reservoir 34 between a closed position, as shown in FIG. 3, in which the closure member 102 inhibits the leakage of working fluid from the reservoir fluid inlet port 100, and an open position. In this embodiment, the closure member 102 is pivotably connected to the fluid reservoir 34. The closure member 102 is locatable within, and forms a fluid-tight seal against, the reservoir fluid inlet port 100. The closure member 102 comprises a head 104 which may be gripped by the user to move the closure member 102 from the closed position to the open position, and which may be pushed by the user towards the reservoir fluid inlet port 100 to return the closure member 102 to the closed position.

The closure member 102 is connected to the fluid reservoir 34 by a pair of arms 106. One end of each arm 106 is connected to the closure member 102, and the other end of each arm 106 is connected to the fluid reservoir 34. In this embodiment, the arms 106 are integral with the closure member 102, with a portion of each arm 106 which is remote from the closure member 102 being connected to the bottom wall 78 of the fluid reservoir 34, for example using an adhesive or by welding. Each arm 106 comprises a hinge 108, which may be formed from a part of the arm 106 which has a locally reduced thickness, to enable the part of the arm 106 which is connected to the closure member 102 to pivot relative to the other part of the arm 106 which is connected to the fluid reservoir 34.

To fill the fluid reservoir 34, the user detaches the cleaning tool 14 from the handle 12, grips the head 104 of the closure member 102 between finger and thumb and pulls it out from the reservoir fluid inlet port 100. The fluid reservoir 34 may then be filled by the user, for example by locating the reservoir fluid inlet port 100 beneath a running tap. Once the fluid reservoir 34 has been filled, the user pushes the head 104 of the closure member 102 back into the reservoir fluid inlet port 100, and reconnects the cleaning tool 14 to the handle 12. The pivoting connection between the closure member 102 and the bottom wall 78 of the fluid reservoir 34 inhibits accidental loss of the closure member 102 while the reservoir fluid inlet port 100 is exposed, and enables the joint between the closure member 102 and the fluid reservoir 34 to be located between the handle 12 and the fluid reservoir 34 when the cleaning tool 14 is mounted on the handle 12. As shown in FIG. 3, the lower parts of the arms 106 of the closure member 102 are located within a recessed section of the bottom wall 78 of the fluid reservoir 34 when the closure member 102 is in its closed position so that the bottom surfaces of the lower parts of the arms 106 are substantially flush with the bottom wall 78 of the fluid reservoir 34.

At least part of the external wall of the fluid reservoir 34 is preferably transparent to allow a user to observe the contents of the fluid reservoir 34, and so assess whether the fluid reservoir 34 requires replenishment prior to the desired use of the appliance 10. The external wall preferably has a shape which is symmetrical about the longitudinal axis of the cleaning tool 14. The external wall preferably has a curved shape, more preferably a convex curved shape, but alternatively the external wall may have a polygonal or faceted shape. In this embodiment, the external wall has a spherical curvature. As described below, the fluid reservoir 34 is mounted on the relatively wide base section 88 of the stem 26, and so the external wall has opposed circular apertures which are centred on the longitudinal axis of the cleaning tool 14 to allow the base section 88 of the stem 26 to pass therethrough.

The fluid reservoir 34 further comprises an inner wall 112 which is connected to the external wall, and which with the external wall defines the capacity of the fluid reservoir 34. The inner wall 112 is tubular in shape. The ends of the inner wall 112 are preferably circular in shape, and are connected to the external wall so as to form a fluid-tight seal between the external wall and the inner wall 112. In this embodiment, the fluid reservoir 34 is formed from two housing parts. A first housing part 114 comprises an upper section of the external wall and the inner wall 112, and so the upper end of the inner wall 112 is integral with an upper section of the external wall. A second housing part 116 comprises a lower section of the external wall and the bottom wall 78 of the fluid reservoir 34.

To mount the fluid reservoir 34 on the stem 26, the circular aperture formed in the first housing part 114 of the fluid reservoir 34 is aligned with the free end of the base section 88 of the stem 26, and the fluid reservoir 34 is pushed on to the stem 26. The internal surface of the inner wall 112 of the fluid reservoir 34 bears against the base section 88 of the stem 26 so that frictional forces therebetween prevent the fluid reservoir 34 from falling from the stem 26. To mount the cleaning tool 14 on the handle 12, the spigot 70 of the handle 12 is aligned with the recess 73 formed in the connector 72 of the cleaning tool 14, and the handle fluid outlet port 82 located adjacent to the spigot 70 is aligned with the cleaning tool fluid inlet port 86 of the cleaning tool 14. The cleaning tool 14 is then pushed on to the spigot 70 so that the handle fluid outlet port 82 connects to the cleaning tool fluid inlet port 86, and so that the fluid reservoir 34 engages the annular seat 76 to connect the reservoir fluid outlet port 80 to the fluid inlet 44 of the fluid delivery system 40. The internal surface of the connector 72 of the stem 26 bears against the external surface of the spigot 70 so that frictional forces therebetween retain the stem 26 on the handle 12. The connector 72 is preferably formed from resilient plastics material which flexes as the connector 72 is pushed on to the spigot 70 to increase the frictional forces therebetween. A spring clip 120 may be provided at least partially about the connector 72 for urging the internal surface of the connector 72 against the spigot 70.

The first part 68 of the fluid delivery system 40 is illustrated in FIGS. 6 to 14. As mentioned above, the first part 68 of the fluid delivery system 68 includes the pump 48 and the motor 50. The pump 48 comprises a pump manifold 130 in which the fluid inlet 56 and the fluid outlet 60 are formed. The pump manifold 130 is connected to a pump housing 132 which defines a chamber 134 for receiving fluid through the fluid inlet 56, and from which fluid is ejected through the fluid outlet 60. The pump 48 comprises a fluid displacement member which is moveable relative to the chamber 134 to draw fluid into the chamber 134 and to urge fluid from the chamber 134 towards the accumulator 62. The fluid displacement member is preferably reciprocally moveable relative to the chamber 134.

In this embodiment, the pump 48 is in the form of a double acting piston pump, in which the fluid displacement member is a piston 136 located in the chamber 134. Alternatively, the pump 48 may be in the form of a diaphragm pump, in which the fluid displacement member is a diaphragm extending across the chamber 134. In such a pump, the diaphragm is moveable, through flexing thereof, between different configurations to pump fluid into and from the chamber 134.

Figure 10:
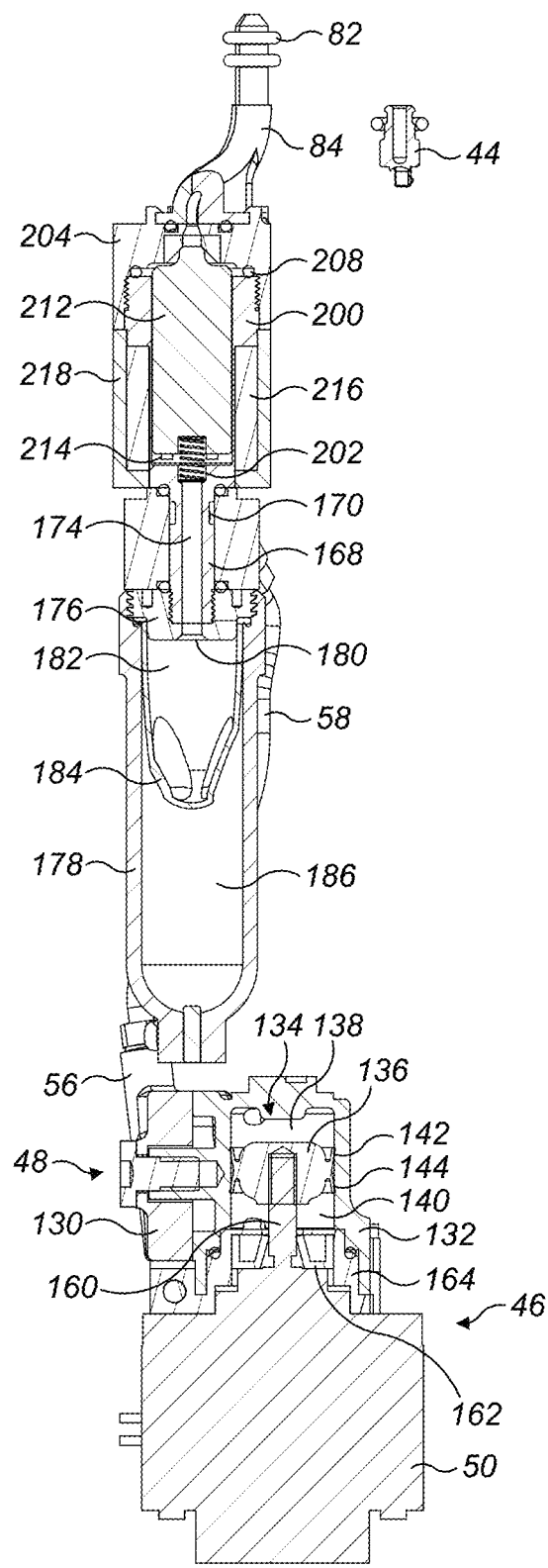
FIG. 10 is a sectional view taken along line D-D in FIG. 7.
Figure 11:
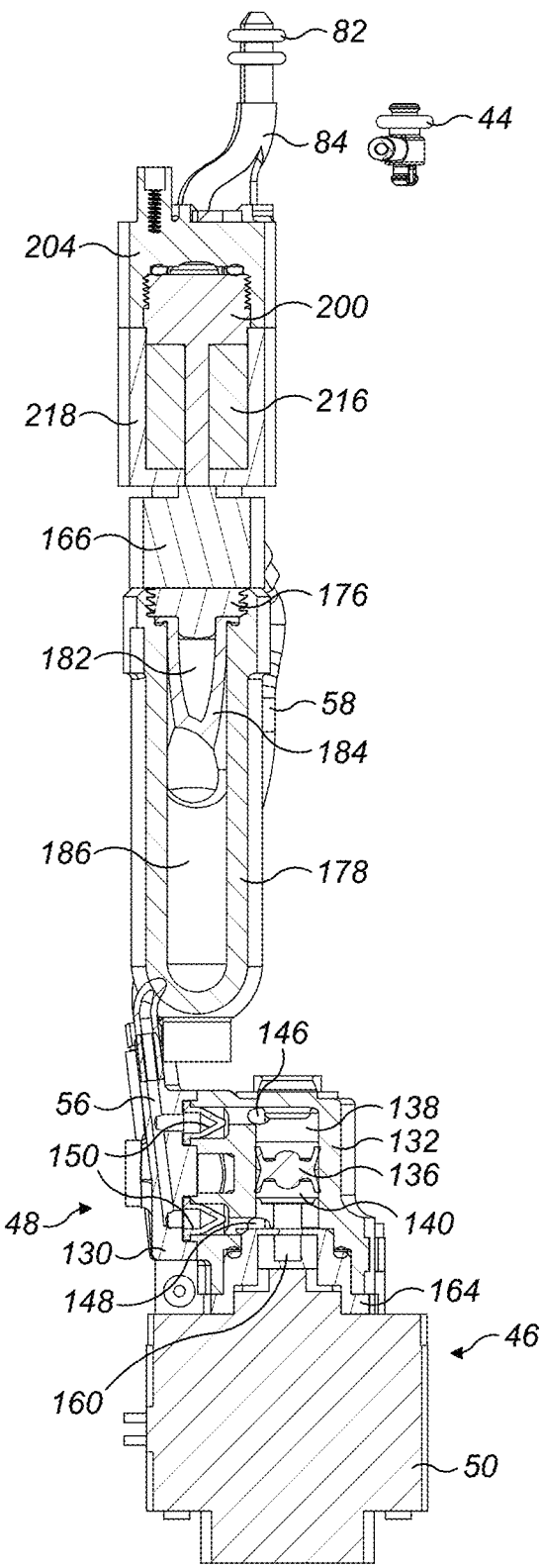
FIG. 11 is a sectional view taken along line E-E in FIG. 7.
Figure 12:
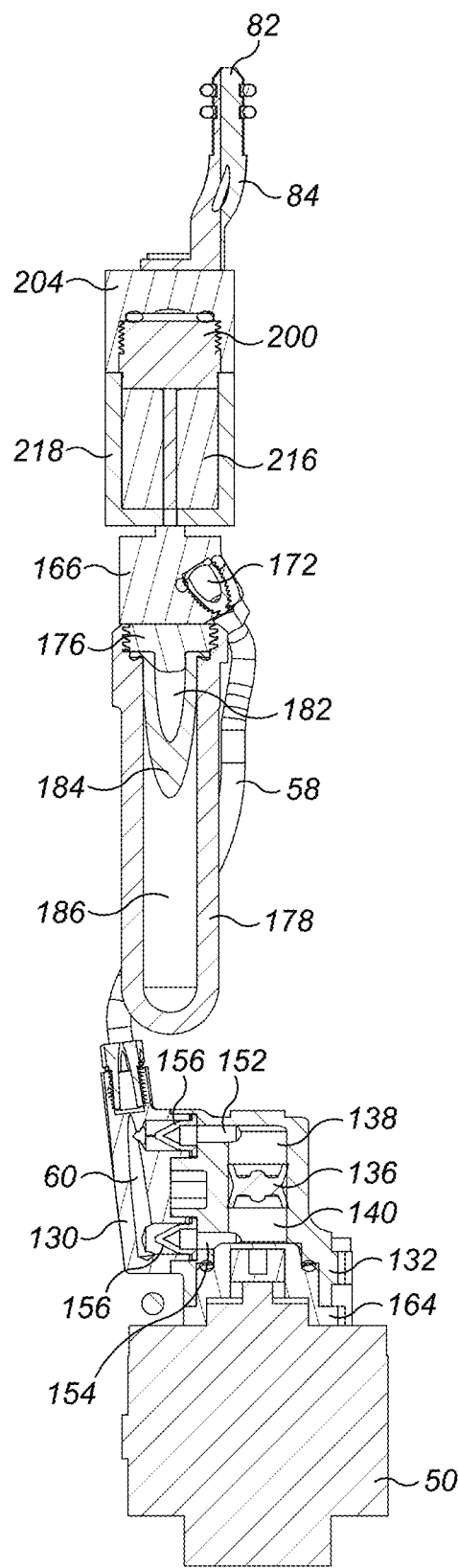
FIG. 12 is a sectional view taken along line F-F in FIG. 7.
Figure 13:
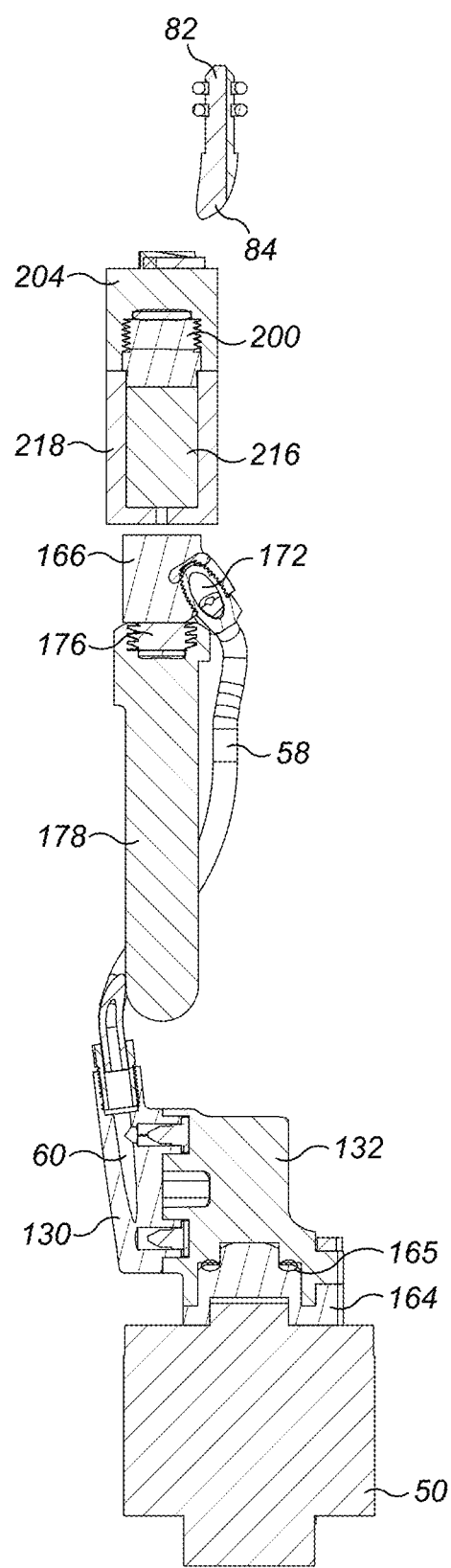
FIG. 13 is a sectional view taken along line G-G in FIG. 7.

With reference to FIG. 10, the piston 136 divides the chamber 134 into a first fluid chamber 138 and a second fluid chamber 140. A first piston seal 142 extends about the piston 136 to form a fluid-tight seal between the piston 136 and the first fluid chamber 138. A second piston seal 144 extends about the piston 136 to form a fluid-tight seal between the piston 136 and the second fluid chamber 140 and the piston 136. In this embodiment, the piston seals 142, 144 are in the form of self-engaging seals extending about the piston 136. With reference to FIG. 11, each of the fluid chambers 138, 140 has a respective fluid inlet port 146, 148 for receiving fluid from the fluid inlet 56 of the pump 48. A one-way valve 150 is located between the fluid inlet 56 and each of the fluid inlet ports 146, 148 or preventing fluid from returning to the fluid inlet 56 from the chamber 134. With reference to FIG. 12, each of the fluid chambers 138, 140 has a respective fluid outlet port 152, 154 for conveying fluid to the fluid outlet 60 of the pump 48. A one-way valve 156 is located between the fluid inlet 56 and each of the fluid outlet ports 152, 154 for preventing fluid from returning to the chamber 134 from the fluid outlet 60. Each of the one-way valves 152, 156 is preferably in the form of a duckbill valve.

The motor 50 is a stepper motor, and in this embodiment is a linear stepper motor which drives a linear actuator, in the form of a drive rod 160, to move the piston 136 reciprocally along a linear path towards and away from the motor 50. As the piston 136 moves towards the motor 50, fluid is drawn into the first fluid chamber 138 from the fluid inlet 56 through fluid inlet port 146. Simultaneously, fluid is urged from the second fluid chamber 140 into the fluid outlet 60 through fluid outlet port 154. As the piston 136 moves away from the motor 50, fluid is urged from the first fluid chamber 138 into the fluid outlet 60 through fluid outlet port 152. Simultaneously, fluid is drawn into the second fluid chamber 140 from the fluid inlet 56 through fluid inlet port 148. An annular shaft seal 162 extends about the drive rod 160 to prevent fluid from leaking from the chamber 134 about the drive rod 160. The shaft seal 162 is disposed within a shaft seal housing 164 located between the motor 50 and the pump housing 132. An O-ring seal 165, indicated in FIG. 13, forms a seal between the pump housing 132 and the shaft seal housing 164.

Figure 14:
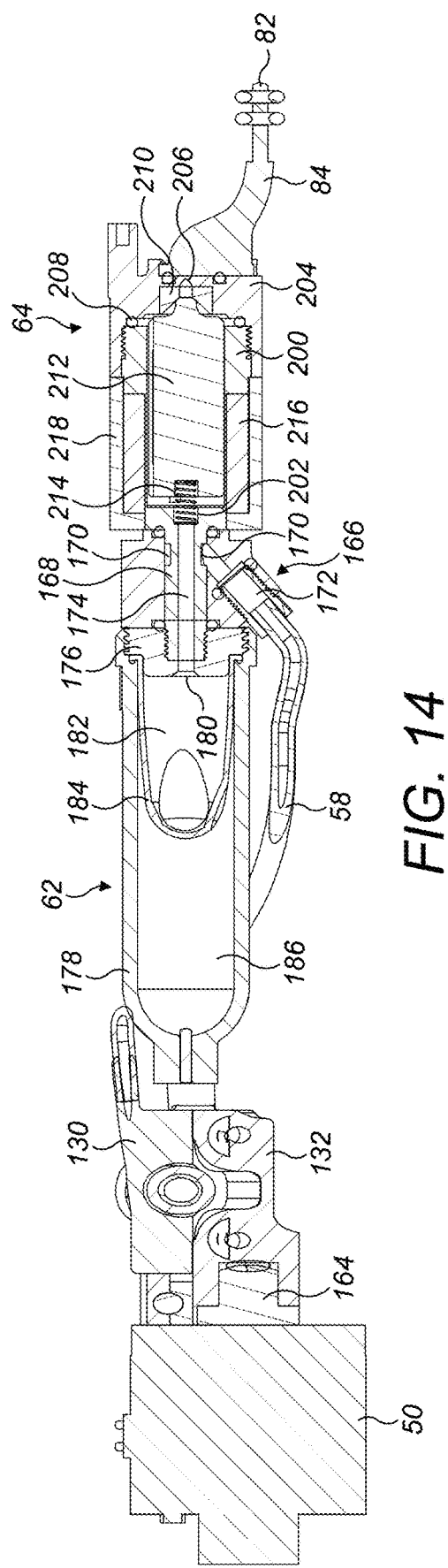
FIG. 14 is a sectional view taken along line H-H in FIG. 9.
Figure 16:
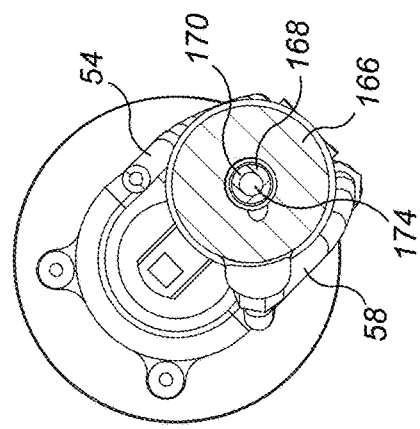
FIG. 16 is a sectional view taken along line L-L in FIG. 9.

Returning to FIG. 6, the second conduit 58 is arranged to convey fluid from the fluid outlet 60 to a banjo fitting 166 located between the accumulator 62 and the solenoid valve 64. With particular reference to FIGS. 14 and 16, the banjo fitting 166 comprises a hollow bolt 168 having a fluid inlet port 170 for receiving fluid from an outlet 172 from the second conduit 58, and for conveying the received fluid into the bore 174 of the bolt 168. A threaded end of the bolt 168 is connected to an end cap 176 of the accumulator 62. The end cap 176 is connected to a housing 178 of the accumulator 62.

In this embodiment, the accumulator 62 is in the form of a gas-charged accumulator. The accumulator 62 comprises a fluid port 180 formed in the end cap 176 for receiving working fluid from one end of the bore 174 of the bolt 168, and for conveying the received working fluid to a fluid chamber 182 of the housing 178. The fluid chamber 182 is delimited by an elastic diaphragm 184 which is urged by a gas-filled chamber 186 towards the fluid port 180, and thus in a direction which urges working fluid from the fluid chamber 182 back through the fluid port 180.

Figure 15:
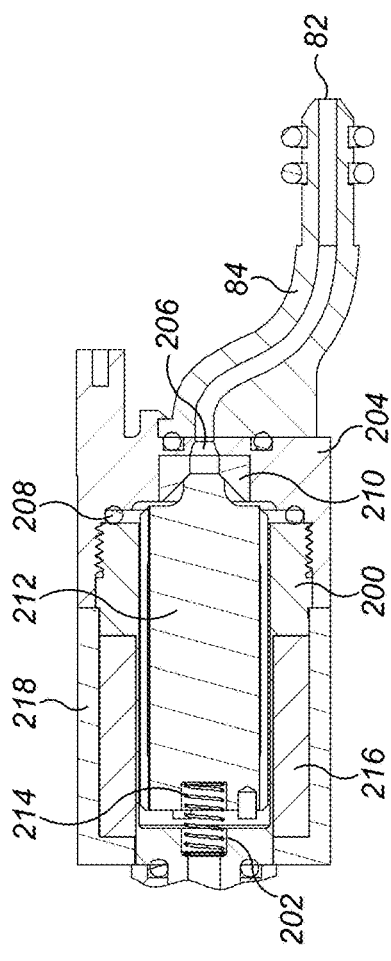
FIG. 15 is a sectional view taken along line J-J in FIG. 9.

The solenoid valve 64 comprises a core housing 200 which is preferably integral with the bolt 168 of the banjo fitting 168. With reference also to FIG. 15, the other end of the bore 174 of the bolt 168 provides a fluid inlet 202 of the solenoid valve 64, and a lower valve housing 204 which comprises a fluid outlet 206 from which fluid passes to the third conduit 84 located in the handle 12. An O-ring 208 forms a seal between the core housing 200 and the lower valve housing 204. The lower valve housing 204 houses a valve seat 210 against which a core 212 is urged by a spring 214 located between the bolt 168 and the core 212. A coil 216 is located around the core housing 200, and a flux conductor 218 is located around the coil 216. The coil 216 is connected to the control circuit 66, which selectively energizes the coil 216 to generate a magnetic field which pulls the core 212 away from the valve seat 210, and so actuate a transition of the solenoid valve 64 from a closed position, as illustrated in FIG. 14, to an open position to allow working fluid to pass from the fluid inlet 202 and around the core 212 to the fluid outlet 206. When the coil 216 is de-energised, the spring 214 urges the core 212 against the valve seat 210 to place the solenoid valve 214 in a closed position. Alternatively, the solenoid valve 64 may be arranged such that the coil 216 is energised to actuate a transition of the solenoid valve 64 from an open position to a closed position.

Figure 17:
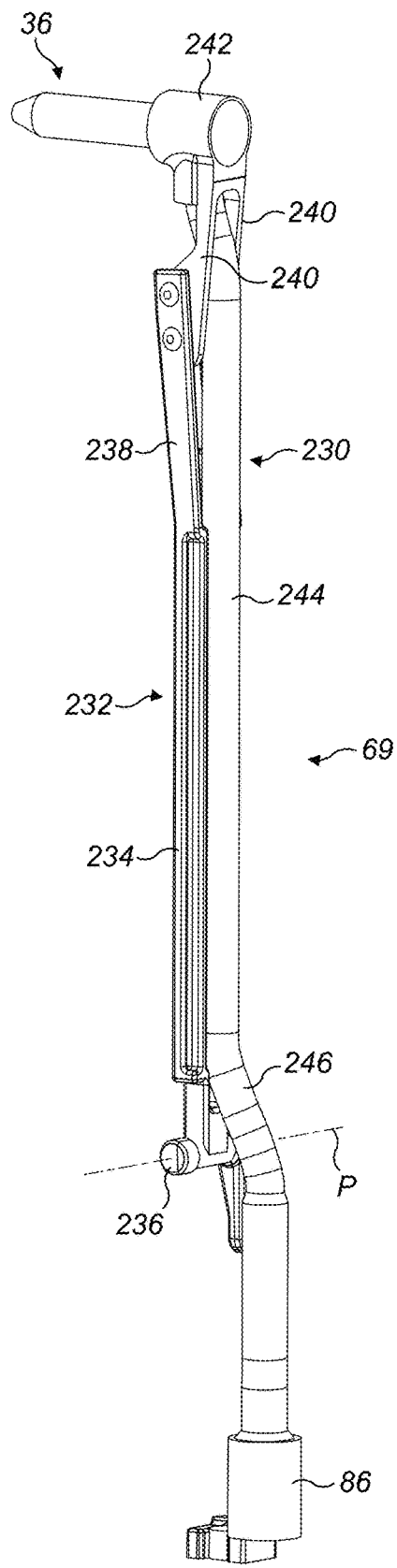
FIG. 17 is a perspective view of a second part of the fluid delivery system which is located in the cleaning tool of the appliance.

Turning to FIG. 17, the cleaning tool fluid inlet port 86 provides a fluid inlet of the second part 69 of the fluid delivery system 40 which is located in the cleaning tool 14. This second part 69 of the fluid delivery system comprises a fluid conduit 230 for conveying fluid from the cleaning tool fluid inlet port 86 to the nozzle 36. The nozzle 36 is mounted on a support 232 which supports the nozzle 36 for movement relative to the handle 12 and to the stem 26 of the cleaning tool 14. The support 232 comprises an elongate body 234 which is connected to the stem 26 for pivoting movement about a pivot axis P. For example, the support 232 may comprise a cylindrical boss 236 which is retained between a pair of spaced recesses formed in the base 88 of the stem 26. Pivot axis P passes through the stem 26, and is substantially orthogonal to the longitudinal axis of the stem 26. The support 232 is generally Y-shaped, having a pair of arms 238 which extend upwardly from the body 134 and which are each connected to a respective leg 240 of the body 142 of the nozzle 36. The fluid conduit 230 passes between the legs 240 of the body 142 of the nozzle 36 to connect to a fluid inlet of the nozzle 36.

The nozzle 36 is moveable relative to the handle 12 between a first, or distal, position, and a second, or proximal, position. In the distal position, the tip of the nozzle 36 protrudes outwardly beyond the ends of the bristles 32, whereas in the proximal position, the tip of the nozzle 36 is retracted relative to the ends of the bristles 32. In this embodiment, the nozzle 36 is biased for movement towards the distal position. The fluid conduit 230 comprises a relatively rigid section 244 which is connected to the nozzle 36, and a relatively flexible section 246 located between the relatively rigid section 244 and the cleaning tool fluid inlet port 86, and which is housed within the stem 26 so as to be in an elastically deformed configuration. The internal force created within the relatively flexible section 246 of the fluid conduit 230 causes the nozzle 36 to pivot about the pivot axis P in such a direction that urges the nozzle 36 towards the distal position relative to the brush unit 29.

In use, the user first fills the fluid reservoir 34 with working fluid, which in this embodiment is water. With the closure member 102 in the open position, the user may place the appliance 10 beneath the spout of a tap and turn on the tap so that water from the spout enters the exposed fluid inlet port 100 of the fluid reservoir 34. As at least part of the external wall of the fluid reservoir 34 is transparent, the user can observe the filling of the fluid reservoir 34. When the fluid reservoir 34 is full, the user returns the closure member 102 to the closed position to seal the fluid inlet port 100.

The user switches on the appliance 10 by depressing button 18, the action of which is detected by the control circuit 66. The user can then select a mode of operation of the appliance 10 by depressing button 20. For example, the user may choose to activate the movement of the brush unit by depressing button 20.

Initially, the control circuit 66 operates the motor 50 to activate the pump 48 to charge the accumulator 62. With the solenoid valve 64 in a closed position, the pump 48 is activated to draw a volume of water from the fluid reservoir 34, and to convey that volume of drawn water to the accumulator 62. As water is received by the fluid chamber 182 of the accumulator 62, the pressure of the water stored within the fluid chamber 182, and thus the pressure of the fluid conveyed to the accumulator 62 by the pump 48, increases. This in turn increases the load on the motor 50 which is driving the pump 48 to convey water to the accumulator 62. As mentioned above, in this embodiment the motor 50 is a stepper motor, preferably a linear stepper motor. The motor 50 will stall when the torque on the motor as it pumps water to the accumulator 62 exceeds an operating limit of the motor 50, which is determined by the design limits of the motor and a current limit set at the motor controller of the control circuit 66. In this embodiment, the motor 50 stalls when the pressure of the pumped fluid is around 6.5 bar (around 650 kPa). The motor controller of the control circuit 66 detects the stalling of the motor 50 from a voltage generated by the motor 50, specifically from measuring the back electromotive force, or back EMF, across a coil or coils of the motor 50. When the stalling of the motor 50 has been detected by the motor controller of the control circuit 66, the control circuit 66 stops the operation of the motor 50 to deactivate the pump 48. In this embodiment, the volume of water which is received by the accumulator each period of time that the pump 48 is activated is around 0.25 ml. The second one-way valves 156 prevent water from returning to the chamber 134 of the pump 48 from the accumulator 62.

A burst of water is emitted from the nozzle 36 in response to user depression of the button 22. The depression of the button 22 is detected by the control circuit 66. The control circuit 66 activates the coil 216 of the solenoid valve 64 to move the solenoid valve 64 to the open position. This allows the diaphragm 184 of the accumulator 62 to move rapidly towards the fluid port 180 to urge the volume of water out from the accumulator 62 in the form of a pressurised burst of water. The time taken to urge that volume of water from the accumulator 62 is preferably in the range from 1 to 50 ms, and in this embodiment is around 30 ms. The burst of water passes though the solenoid valve 64 and the fluid conduits 84, 230 to be ejected from the fluid outlet 42 of the nozzle 36. When the nozzle 36 is positioned within or aligned with an interproximal gap, the burst of water ejected from the nozzle 36 can dislodge matter located within the interproximal gap.

The control circuit 66 is arranged to replenish the accumulator 62 following the delivery of the burst of water to the nozzle 36. The control circuit 66 is arranged to move the solenoid valve 64 to the closed position, and to operate the motor 50 to activate the pump 48 to convey another volume of water from the fluid reservoir 34 to the accumulator 62. The control circuit 66 is configured to disable the opening of the solenoid valve 64, in response to the user depression of the button 22, until the accumulator 62 has become fully replenished with water, and so preferably for a period of around 500 ms after the last burst of water was ejected from the nozzle 36.

In the above embodiment, the capacity of the fluid chamber 182 of the accumulator 62 is substantially the same as the volume of a single burst of working fluid. However, the capacity of the fluid chamber 182 may be larger than the volume of a single burst of working fluid.

In a second embodiment, the fluid chamber has a capacity of 0.75 ml, and a single burst of working fluid has a volume of around 0.25 ml. In this second embodiment, when in its third condition the control circuit 66 is arranged to hold the solenoid valve 64 in an open position for a time period which allows only the required volume of working fluid to be ejected from the accumulator 62 to form a single burst of working fluid. For example, the solenoid valve 64 may be held in an open position for a time period of 30 ms to allow a single burst of working fluid having a volume of 0.25 ml to be delivered to the nozzle 36. The control circuit 66 returns to its first condition following the ejection of that single burst of working fluid. In this case, and provided that there is sufficient working fluid in the accumulator 62 to deliver those three bursts of working fluid to the nozzle 36, the control circuit 66 is arranged to replenish the accumulator 62 following the delivery of every third burst of working fluid to the nozzle 36.

In a third embodiment, the fluid chamber has a capacity of 0.25 ml, and a single burst of working fluid has a volume of around 0.08 ml. Similar to the second embodiment, in this third embodiment the control circuit 66 is arranged to hold the solenoid valve 64 in an open position for a time period which allows only the required volume of working fluid to be ejected from the accumulator 62 to form a single burst of working fluid. For example, the solenoid valve may be held in an open position for a time period of around 10 ms to allow a single burst of working fluid having a volume of 0.08 ml to be delivered to the nozzle 36. Again, in this case the control circuit 66 is arranged to replenish the accumulator 62 following the delivery of every third burst of working fluid to the nozzle 36, but the time required to replenish the accumulator 62 in this third embodiment is shorter than the time required to replenish the accumulator 62 in the second embodiment.

In each of the first to third embodiments, the control circuit 66 is arranged to deliver a single burst of working fluid depending on a received input, such as the depression of the button 22. However, the control circuit 66 may be arranged to deliver a series of bursts of working fluid depending on such a received input. Each of the bursts of working fluid within a series preferably contains substantially the same volume of working fluid.

In a fourth embodiment, the fluid chamber 182 of the accumulator 62 has a capacity of 0.25 ml, and the control circuit 66 is arranged to control the fluid delivery system 100 to deliver a single series of three bursts of working fluid, each having a volume of around 0.08 ml, in response to user depression of the button 22. The depression of the button 22 is detected by the control circuit 66. The control circuit 66 activates the coil 216 of the solenoid valve 64 to move the solenoid valve 64 to the open position. The control circuit 66 holds the solenoid valve 64 in the open position only for a time period which allows the diaphragm of the accumulator 62 to urge a volume of water from the accumulator 62 to form the first pressurised burst of water. In this embodiment, the time taken to urge that volume of water from the accumulator 62 is around 10 ms, and so after that period of time the control circuit 66 deactivates the coil 216 of the solenoid valve 64 to allow the solenoid valve 64 to move to the closed position.

Once the solenoid valve 64 is in the closed position, the control circuit 66 re-activates the coil 216 of the solenoid valve 64 to move the solenoid valve 64 back to the open position. Again, the control circuit 66 holds the solenoid valve 64 in the open position only for a time period which allows the diaphragm of the accumulator 62 to urge a second volume of water from the accumulator 62 to form the second pressurised burst of water, and so in this embodiment a second time period of around 10 ms.

After that period of time has elapsed, the control circuit 66 deactivates the coil 216 of the solenoid valve 64 to allow the solenoid valve 64 to move to the closed position. Once the solenoid valve 64 is in the closed position, the control circuit 66 again re-activates the coil 216 of the solenoid valve 64 to move the solenoid valve 64 back to the open position. Once again, the control circuit 66 holds the solenoid valve 64 in the open position only for a time period which allows the diaphragm of the accumulator 62 to urge a third volume of water from the accumulator 62 to form the third pressurised burst of water, and so in this embodiment a third time period of around 10 ms. After that period of time has elapsed, the control circuit 66 deactivates the coil 216 of the solenoid valve 64 to allow the solenoid valve 64 to move to the closed position. The pump 48 is then operated to replenish the accumulator 62.

Within a series, the time period between successive bursts of working fluid is preferably equal, and is preferably in the range from 1 to 25 ms, more preferably in the range from 2 to 10 ms, so that the entire series of bursts may be delivered to a single interproximal gap. This can allow for a slight variation in the position of the tip of the nozzle 36 relative to interproximal gap with each successive burst, and so potentially improving the removal of material from within the interproximal gap.

In this fourth embodiment, the capacity of the fluid chamber 182 of the accumulator 62 is substantially the same as the volume of working fluid which is ejected from the nozzle 36 in a single series of bursts of working fluid. Alternatively, the capacity of the fluid chamber 182 of the accumulator 62 may be greater than the volume of working fluid which is ejected from the nozzle 36 in a single series of bursts of working fluid. For example, in a fifth embodiment, the capacity of the fluid chamber 182 is increased to 0.75 ml, but the control circuit 66 is arranged to eject the same, single series of three bursts of working fluid, each having a volume of around 0.08 ml, in response to user depression of the button 22. Therefore, in this fifth embodiment the accumulator 62 requires replenishment following the delivery of three series of bursts of working fluid from the appliance 10.

The invention claimed is:

1. A dental cleaning appliance comprising:
   a fluid delivery system comprising a fluid inlet, a pump for drawing a working fluid through the fluid inlet, a drive for actuating the pump, and a nozzle having a fluid outlet for ejecting working fluid from the appliance; and
   wherein the drive comprises a motor and a control circuit for operating the motor, and wherein the control circuit is configured to detect stalling of the motor from a voltage generated by the motor and to deactivate the motor when stalling of the motor has been detected.

2. The appliance of claim 1, wherein the control circuit is configured to detect stalling of the motor by measuring a back electromotive force across a coil of the motor.

3. The appliance of claim 1, wherein the motor is configured to stall when the pressure of pumped working fluid is in the range from 3 to 10 bar, preferably in the range from 5 to 8 bar.

4. The appliance of claim 1, wherein the drive comprises a linear actuator coupled to the motor, wherein the control circuit is configured to drive the motor to move the actuator.

5. The appliance of claim 1, wherein the motor is a stepper motor.

6. The appliance of claim 5, wherein the motor is a linear stepper motor.

7. The appliance of claim 1, wherein the pump is a piston pump.

8. The appliance of claim 1, wherein the pump is a double acting pump.

9. The appliance of claim 1, comprising a fluid chamber for receiving working fluid from the pump.

10. The appliance of claim 9, wherein the fluid chamber has a capacity in the range from 0.1 to 1 ml.

11. The appliance of claim 9, comprising a hydraulic accumulator, and wherein the accumulator comprises said fluid chamber.

12. The appliance of claim 11, wherein the accumulator is a gas-charged accumulator.

13. The appliance of claim 10, comprising a valve having an open position for enabling a burst of working fluid to be delivered from the fluid chamber to the nozzle and a closed position for enabling the fluid chamber to be replenished under the action of the pump.

14. The appliance of claim 13, wherein the valve is located downstream from the fluid chamber.

15. The appliance of claim 13, wherein the valve is a solenoid valve.

16. The appliance of claim 1, comprising a fluid reservoir for storing working fluid, and wherein the pump is arranged to draw working fluid from the fluid reservoir.

17. The appliance of claim 16, wherein the fluid reservoir has a capacity in the range from 5 to 50 ml.

18. A dental cleaning appliance comprising:
a fluid reservoir for storing working fluid;
a fluid delivery system comprising a fluid inlet, a pump for drawing the working fluid from the fluid reservoir through the fluid inlet, a drive for actuating the pump, and a nozzle having a fluid outlet for ejecting working fluid from the appliance; and
wherein the drive comprises a motor and a control circuit for operating the motor, and wherein the control circuit is configured to detect stalling of the motor and to deactivate the motor when stalling of the motor has been detected.

19. The appliance of claim 18, wherein the fluid reservoir has a capacity in the range from 5 to 50 ml.

20. The appliance of claim 18, wherein the control circuit is configured to detect stalling of the motor from a voltage generated by the motor.

21. The appliance of claim 20, wherein the control circuit is configured to detect stalling of the motor by measuring a back electromotive force across a coil of the motor.

22. The appliance of claim 18, wherein the motor is configured to stall when the pressure of pumped working fluid is in the range from 3 to 10 bar, preferably in the range from 5 to 8 bar.

23. The appliance of claim 18, wherein the drive comprises a linear actuator coupled to the motor, wherein the control circuit is configured to drive the motor to move the actuator.

24. The appliance of claim 18, wherein the motor is a stepper motor.

25. The appliance of claim 24, wherein the motor is a linear stepper motor.

26. The appliance of claim 18, wherein the pump is a piston pump.

27. The appliance of claim 18, wherein the pump is a double acting pump.

28. The appliance of claim 18, comprising a fluid chamber for receiving working fluid from the pump.

29. The appliance of claim 28, wherein the fluid chamber has a capacity in the range from 0.1 to 1 ml.

30. The appliance of claim 28, comprising a hydraulic accumulator, and wherein the accumulator comprises said fluid chamber.

31. The appliance of claim 30, wherein the accumulator is a gas-charged accumulator.

32. The appliance of claim 29, comprising a valve having an open position for enabling a burst of working fluid to be delivered from the fluid chamber to the nozzle and a closed position for enabling the fluid chamber to be replenished under the action of the pump.

33. The appliance of claim 32, wherein the valve is located downstream from the fluid chamber.

34. The appliance of claim 32, wherein the valve is a solenoid valve.

* * * * *